US006629466B2

United States Patent
Grote et al.

(10) Patent No.: US 6,629,466 B2
(45) Date of Patent: Oct. 7, 2003

(54) TEST SPECIMEN HOLDER

(75) Inventors: Vogel P. Grote, Jordan, MN (US); Paul M. Krueger, New Hope, MN (US); Bradley D. Schulz, Savage, MN (US); Andrew B. Geppert, Blaine, MN (US); Jason D. Holm, St. Louis Park, MN (US)

(73) Assignee: MTS Systems Corporation, Eden Prairie, MN (US)

( * ) Notice: Subject to any disclaimer, the term of this patent is extended or adjusted under 35 U.S.C. 154(b) by 0 days.

(21) Appl. No.: 09/851,800

(22) Filed: May 9, 2001

(65) Prior Publication Data

US 2002/0166387 A1 Nov. 14, 2002

(51) Int. Cl.[7] .................................................. G01N 3/02
(52) U.S. Cl. ........................................................ 73/857
(58) Field of Search .......................... 73/856, 857–858, 73/859, 860

(56) References Cited

U.S. PATENT DOCUMENTS

| | | | | |
|---|---|---|---|---|
| 4,019,378 A | * | 4/1977 | Keller et al. ............... | 279/4.11 |
| 4,026,145 A | * | 5/1977 | Nagy et al. .................... | 73/857 |
| 4,537,080 A | * | 8/1985 | Christiansen ................. | 73/854 |
| 5,095,757 A | * | 3/1992 | Larsen et al. ................. | 73/857 |
| 5,581,040 A | * | 12/1996 | Lin .............................. | 73/833 |
| 5,948,994 A | * | 9/1999 | Jen et al. ...................... | 73/796 |

OTHER PUBLICATIONS

Photo of Grip manufactured by Adamel Lhomargy of Paris, France, sold prior to May 9, 2000.
Photo of Grip manufactured by Instron Corporation of Canton, MA, sold prior to May 9, 2000.

* cited by examiner

*Primary Examiner*—Max Noori
(74) *Attorney, Agent, or Firm*—Westman, Champlin & Kelly, P.A.; S. Koehler

(57) ABSTRACT

A test specimen holder for holding a test specimen in a material testing machine includes a base member having a piston chamber, a valve chamber fluidly coupled to the piston chamber, a port fluidly coupled to the valve chamber and an end couplable to a material testing machine. A piston is movable relative to the piston chamber. A pair of first and second jaw assemblies are supported by the base members so as to be opposite each other. The jaw assemblies are operably coupled to the piston. A valve is disposed in the valve chamber and a valve stem is coupled to the valve. The valve stem is supported by the base member and is twistable to operate the valve. A user operable knob is coupled to the valve stem.

9 Claims, 8 Drawing Sheets

TEST SPECIMEN HOLDER

BACKGROUND OF THE INVENTION

The present invention relates to a material testing system that applies force loads to a test specimen. More particularly, the present invention relates to a test specimen holder that holds the test specimen in the material testing system.

Test specimen holders or grips are well known in the material testing art and are used frequently to hold a test specimen in a material testing system. The holder includes opposed jaws operated by a piston that grips the test specimen therebetween. Preferably, the jaws grip the test specimen without altering the vertical position of the jaws on the test specimen, thereby making it possible to preselect the exact point at which the specimen will be held in order not to impart tension loads during placement of the test specimen in the material testing system.

Fluid pressure (hydraulic or pneumatic) pressurizes the piston chamber to operate the jaws. On some known test specimen holders, operation of the valve can apply unwanted loads to the test specimen. For instance, many test specimen holders utilize a toggle-type switch to control the valve providing fluid pressure to the piston chamber. In some cases, the amount of force required to operate the switch and the direction in which the force is applied may cause unwanted preloading of the test specimen due to small displacements of the test specimen holder.

SUMMARY OF THE INVENTION

A testing specimen holder for holding a test specimen in a material testing machine includes a base member having a piston chamber, a valve chamber fluidly coupled to the piston chamber, and a port fluidly coupled to the valve chamber. A piston is moveable relative to the piston chamber. First and second jaw assemblies are supported by the base member so as to be opposite each other. The jaw assemblies are operably coupled to the piston. A valve is disposed in the valve chamber and a valve stem is coupled to the valve. The valve stem is supported by the base member and is twistable to operate the valve. A user operable knob is coupled to the valve stem.

DETAILED DESCRIPTION OF THE ILLUSTRATIVE EMBODIMENTS

Figure 1:
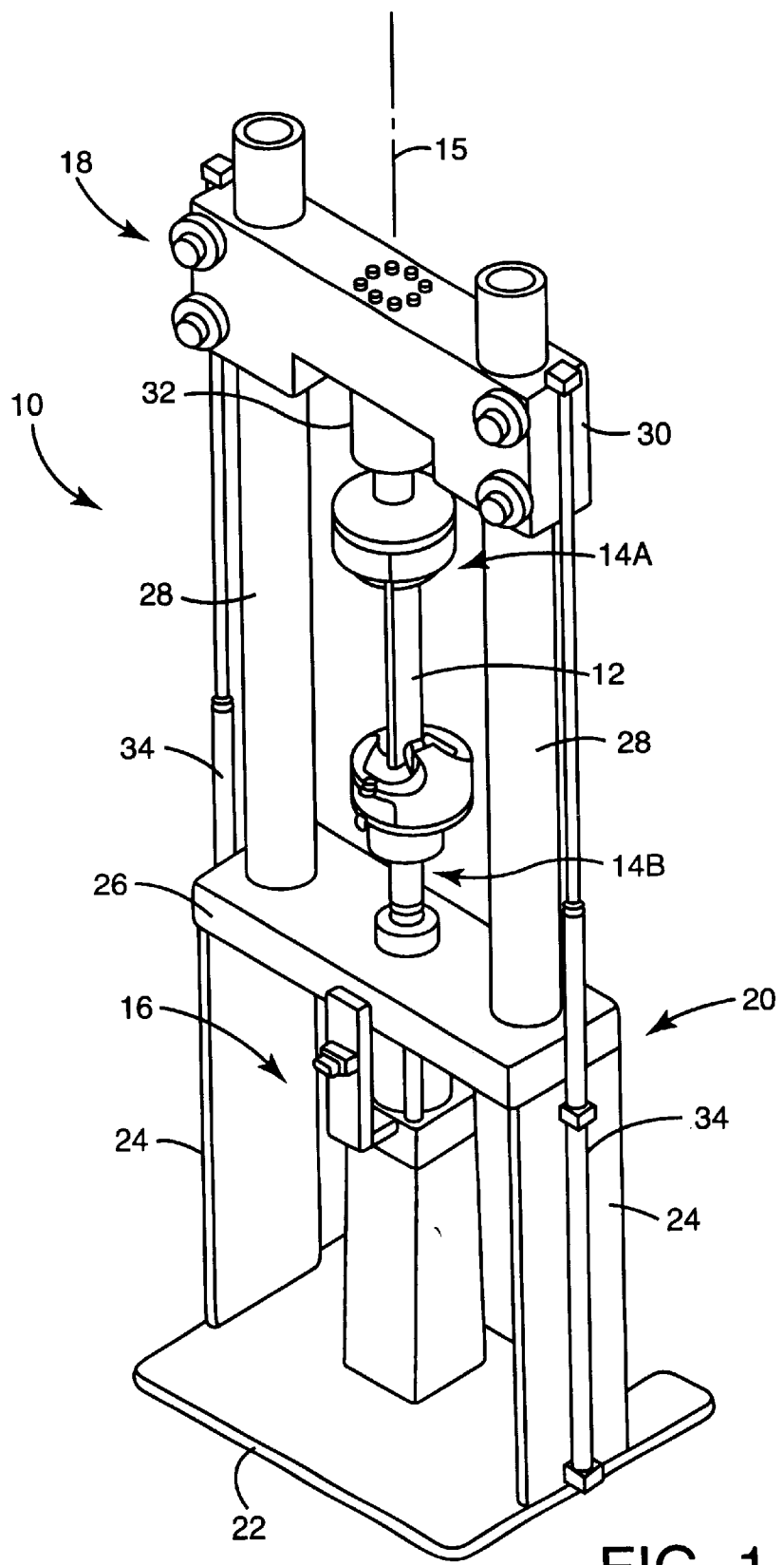
FIG. 1 is a perspective view of a material testing system having a test specimen holder of the present invention.

A material testing system 10 for applying force loads to a test specimen 12 is illustrated in FIG. 1. The system 10 includes an upper grip 14A and a lower grip 14B of the present invention that hold the test specimen 12 along a longitudinal axis 15. The lower grip 14B is connected to an actuator 16, herein a hydraulic actuator, through which force loads are provided to the test specimen 12 and reacted against a reaction structure generally indicated at 18. In the embodiment illustrated, the material testing system 10 includes a frame 20 having a base 22. A pair of support members 24 extend upwardly from the base 22 and are joined together by a crossbeam 26 which provides a stable support surface. A pair of support columns 28 extend upwardly from the crossbeam 26 to a movable crosshead 30. A load cell or force transducer 32 joins the upper grip 14A to the crosshead 30. As is known in the art, the load cell 32 provides a representative signal indicative of tension and compression forces applied to the test specimen 12. The crosshead 30 and the support columns 28 provide the reaction structure 18. Hydraulic lifts 34 move the crosshead 30 to selectively fixed positions.

Figure 2:
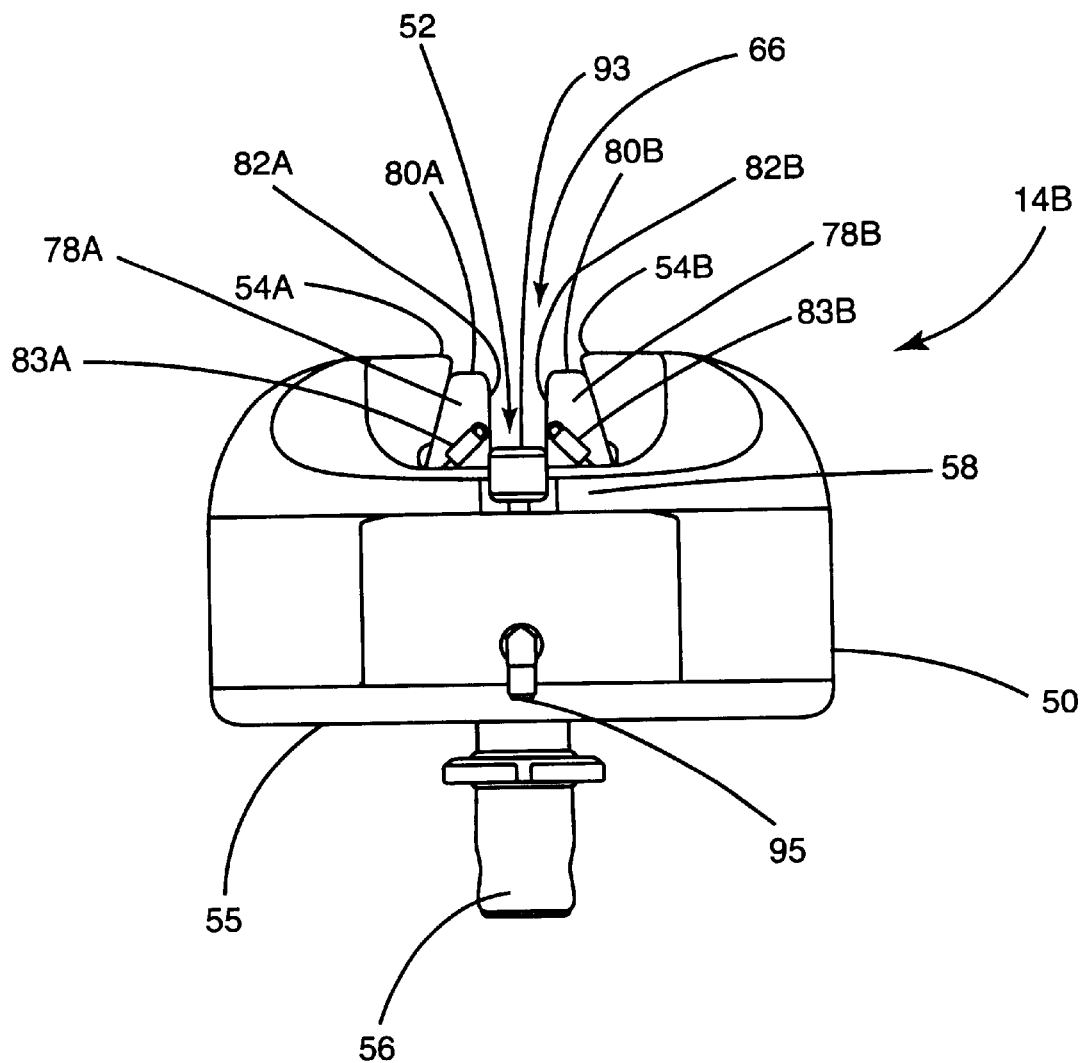
FIG. 2 is a front view of the test specimen holder in a first position.
Figure 3:
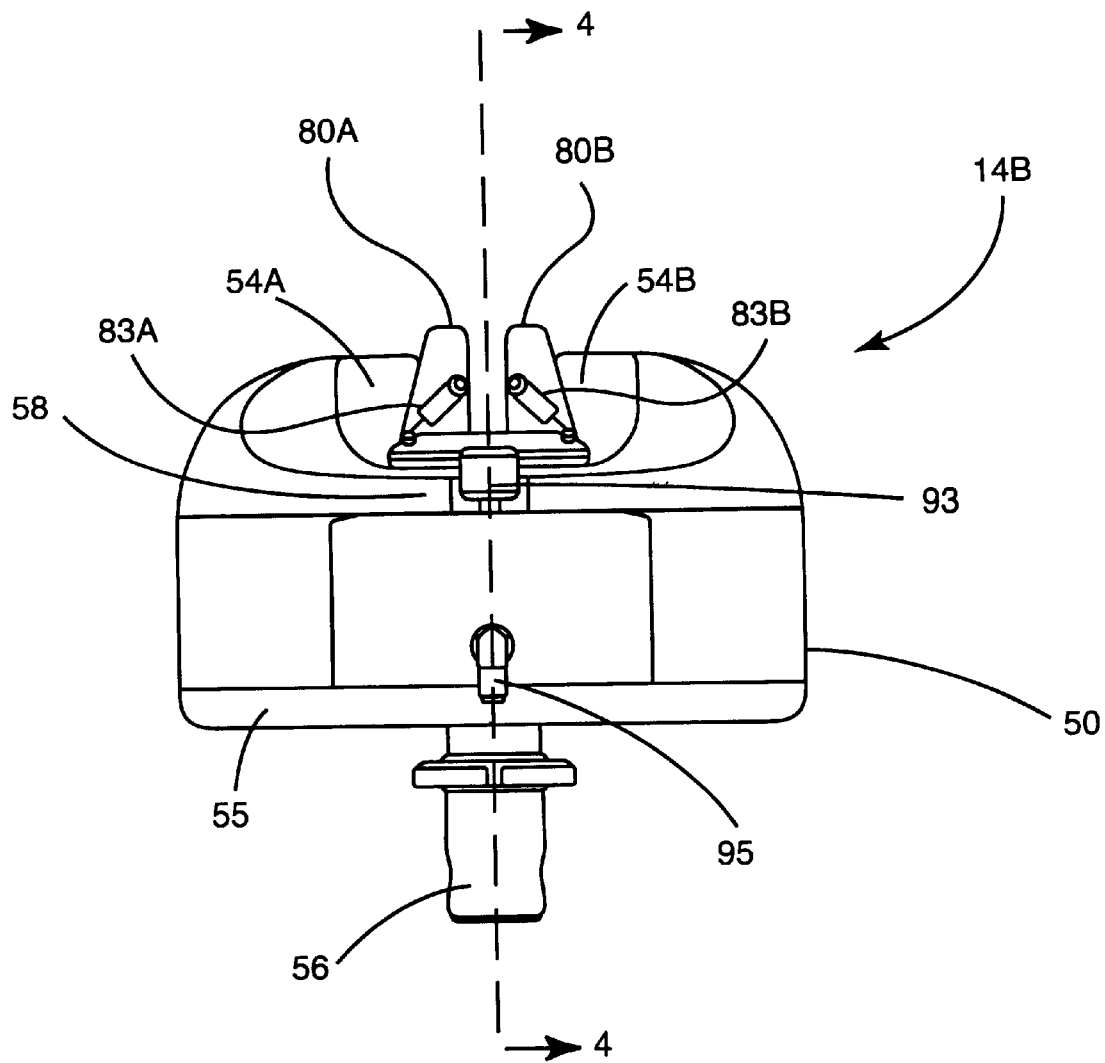
FIG. 3 is a front view of the test specimen holder in a second position.

Referring to FIGS. 2 and 3 and the lower grip 14B by way of example, the lower grip 14B includes a support frame 50 having a recess 52 for receiving the test specimen 12. The recess 52 is formed from a first sidewall portion 54A and a second sidewall portion 54B that converge toward each other on opposite sides of the longitudinal axis 15 of the test specimen 12. Grip 14B also includes end plate 55 and alignment member 56. Alignment member 56 has an end which is couplable to the testing system 10. Port 95 is also couplable to system 10 to provide fluid into base member 50. User operable knob 93 is operably coupled to port 95 and selectively applies fluid into and out of base member 50.

Figure 5:
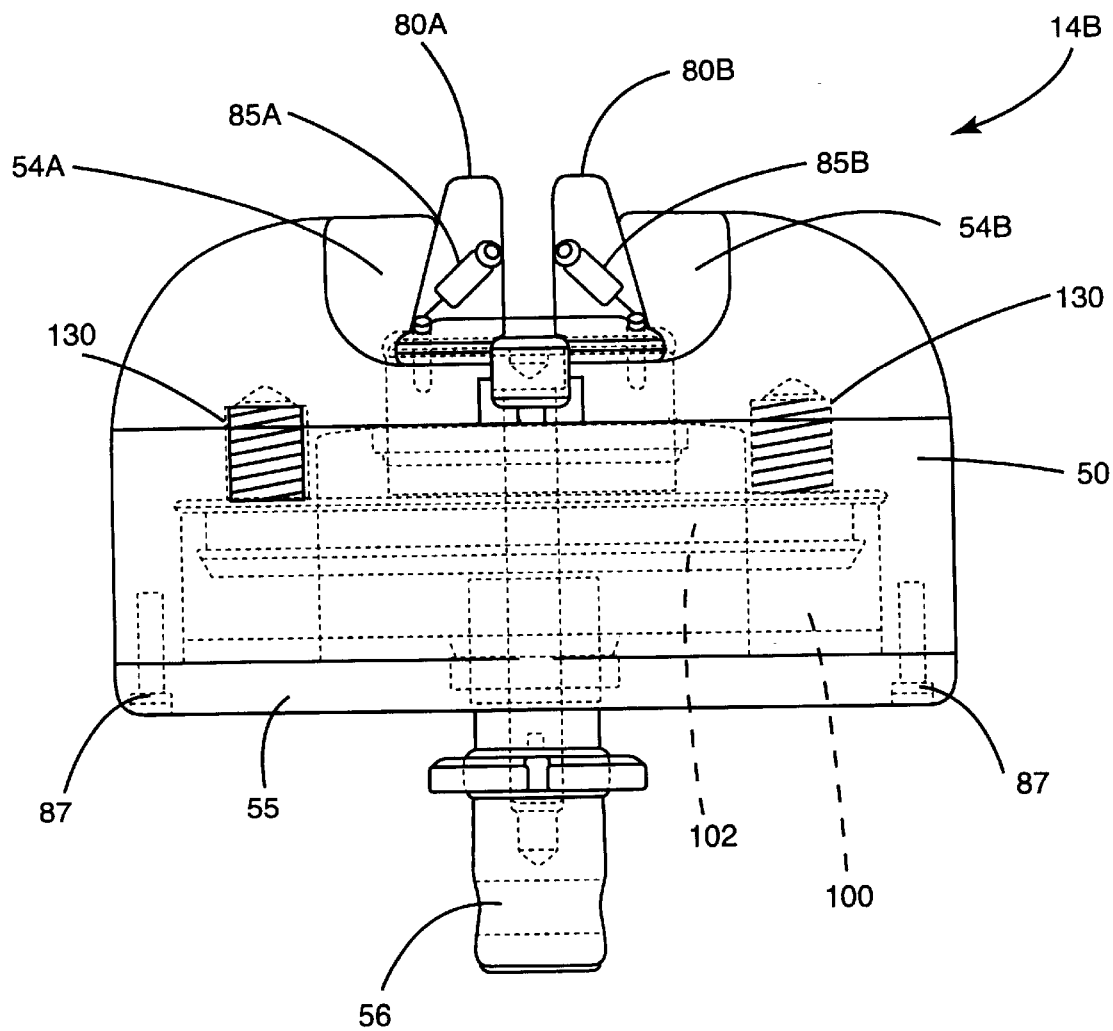
FIG. 5 is a rear view of the test specimen holder in the second position.

Jaw assemblies 78A and 78B are adapted to grip test specimen 12 during mechanical testing upon operation of user operable knob 93. Jaw assemblies 78A and 78B include a first jaw 80A and a second jaw 80B, respectively. The jaws 80A and 80B are disposed in the recess 52. The first jaw 80A engages and is slidable upon an inner surface of the first side wall portion 54A. The second jaw 80B engages and is slidable upon an inner surface of the second sidewall portion 54B. Each jaw 80A and 80B includes a gripping surface 82A and 82B, respectively, that engage the test specimen 12 when located therebetween. As best illustrated in FIG. 2, the recess 52 has a continuous access aperture 66 through which test specimen 12 can be inserted to be engaged by jaws 80A and 80B. Springs 83A and 83B are provided to slidably actuate jaws 80A and 80B relative to each other upon inner surfaces of side wall portions 54A and 54B, respectively. In addition, similar springs are provided on opposite sides of jaws 80A and 80B as illustrated in FIG. 5.

Ultimately, operation of jaws 80A and 80B is controlled by the user operable knob 93. User operable knob 93 controls the amount of fluid through port 95 and thus pressurization of a chamber in base member 50. The jaws 80A and 80B are illustrated in FIG. 2 to be in an open position. A user may then place specimen 12 in access aperture 66. Upon operation of the user operable knob 93, jaws 80A and 80B move to a closed position, as illustrated in FIG. 3, in order to engage test specimen 12.

Figure 4:
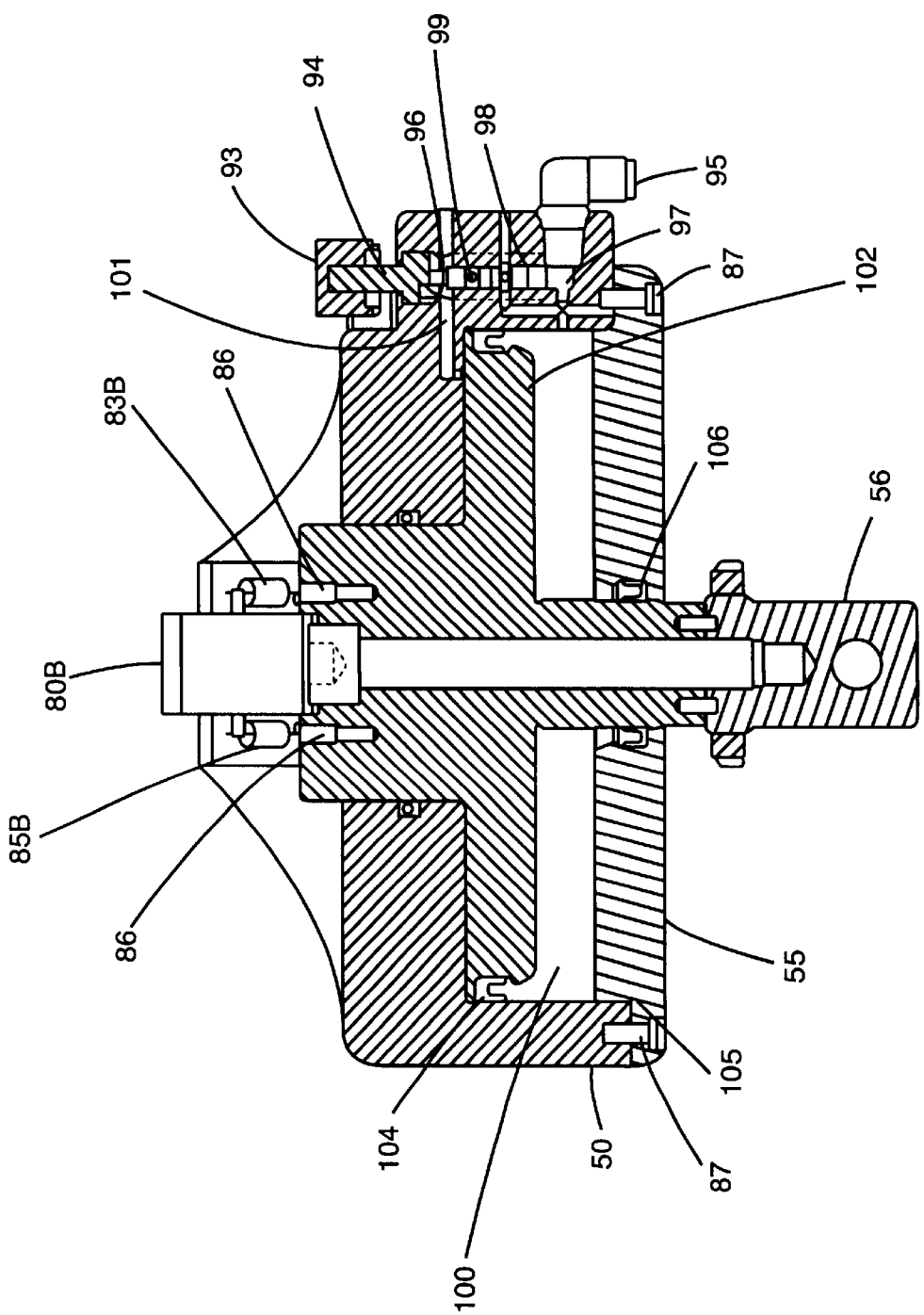
FIG. 4 is a section view of the test specimen holder taken along line 4—4 in FIG. 3.

FIG. 4 illustrates a cross section of grip 14B taken along the line 4—4 of FIG. 3. A piston chamber 100 is provided in base member 50. In the embodiment illustrated, end plate 55 is coupled to base member 50 with fasteners 87 and encloses piston chamber 100. Piston 102 is moveable relative to the piston chamber 100 upon changes in fluid pressure in piston chamber 100. Seals 104, 105 and 106 are provided to prevent unwanted entry or exit of fluid from piston chamber 100. It should be noted that the construction of piston chamber 100 is but one exemplary embodiment. In general, the present invention can be used with any form of piston chamber.

Figure 6:
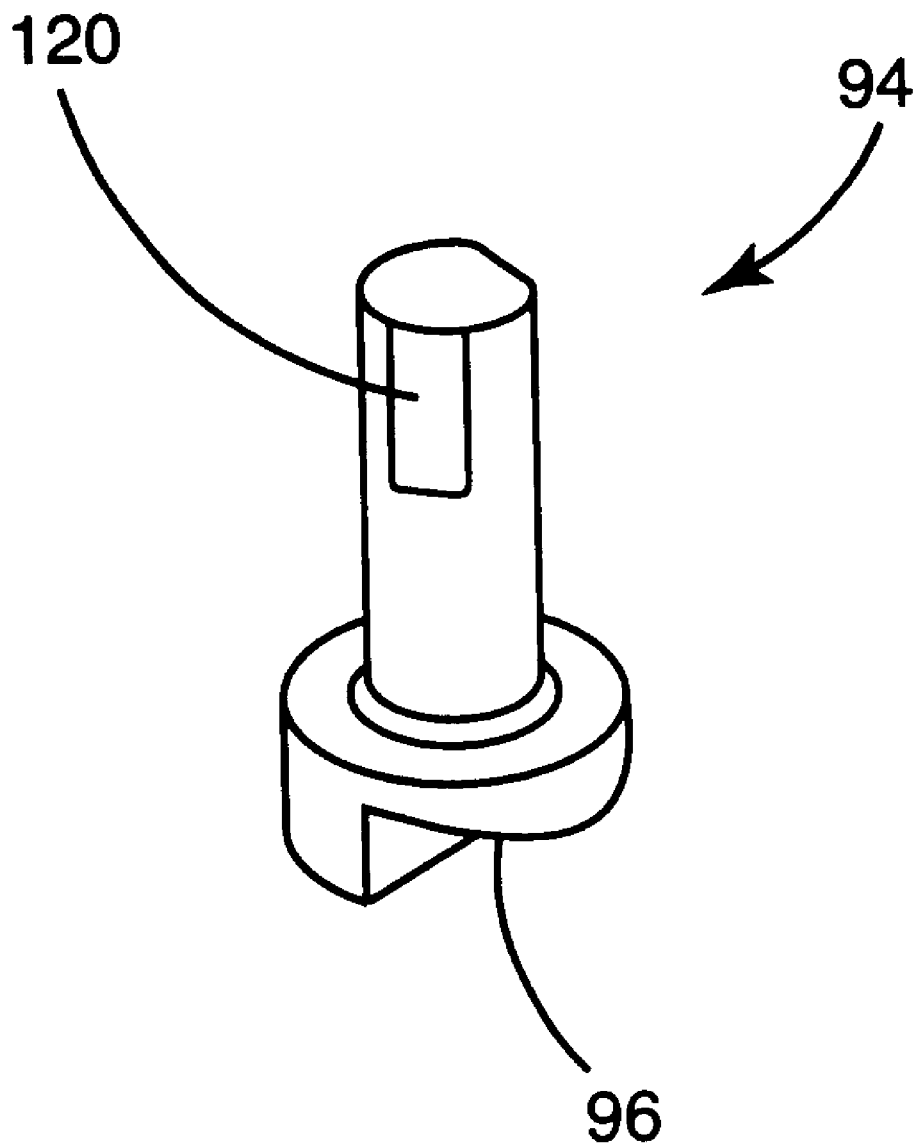
FIG. 6 is an exemplary valve stem for use in the present invention.

User operable knob 93 is coupled to valve stem 94 in order to actuate valve 98. Valve stem 94 has a cam surface 96 that engages valve 98 disposed in valve chamber 97. As illustrated, valve chamber 97 is fluidly coupled to piston chamber 100 and port 95 is fluidly coupled to the valve chamber 97. With reference also to FIG. 6, valve stem 94 engages valve 98 such that upon operation of user operable knob 93, valve 98 is linearly displaced within valve chamber 97. Generally, valve 98 can be in an open or a closed position. In an open position, fluid is allowed to pass from port 95 through valve chamber 97 and into piston chamber 100. When valve 98 is in a closed position, valve 98 is arranged such that vent 99 allows fluid to exit the piston chamber 100 through manifold exit port 101.

Changes in fluid pressure within piston chamber 100 moves piston chamber 100 relative to piston 102 depending on the position of valve 98. Increased fluid from port 95 to piston chamber 100 urges base member 50 to move in a direction away from jaws 80A and 80B. This, in turn, causes jaws 80A and 80B to move toward each other. To release the test specimen, user operable knob 93 is actuated to allow fluid to exit through vent 99 and manifold exit port 101. Reduced pressure within piston chamber 100 causes the base member 50 to move toward jaws 80A and 80B. Springs 83A, 83B, 85A and 85B urge the jaws 80A and 80B away from each other.

FIG. 5 is a rear view of the test specimen holder in the closed position as illustrated in FIG. 3. Certain elements are illustrated with dashed lines in FIG. 5 in order to further describe operation of piston 102. In this embodiment, resilient members 130 (e.g. springs) are provided in base member 50 in order to urge base member 50 toward jaws 80A and 80B. Thus, when user operable knob 93 (FIG. 3) is operated to open jaws 80A and 80B, resilient members 130 assist in urging base member 50 toward jaws 80A and 80B. As a result, resilient members 130 and springs 83A, 83B, 85A and 85B uniformly move jaws 80A and 80B to an open position as shown in FIG. 2.

FIG. 6 illustrates an exemplary valve stem for use in the present invention. As illustrated, valve stem 94 includes cam surface 96 adapted to engage valve 98 as illustrated in FIG. 4. Valve stem also includes notch 120 that is adapted to engage user operable knob 93. Thus, upon operation of user operable knob 93, valve stem 94 is twistable, allowing cam surface 96 to engage valve 98 in order to operate valve 98. The force necessary to twist the knob 93 is reacted through base member 50 to a combination of force transducer 32 and test specimen 12. More importantly though, the twisting nature of knob 93 minimizes any forces imparted to test specimen 12 and force transducer 32, thereby minimizing any unwanted preloading that would be applied to test specimen 12 during loading in the test specimen holders 14A and 14B. Orientation of value 98 and valve stem 94 herein is parallel to the axis extending through specimen 12 although other orientations can be used.

Figure 7:
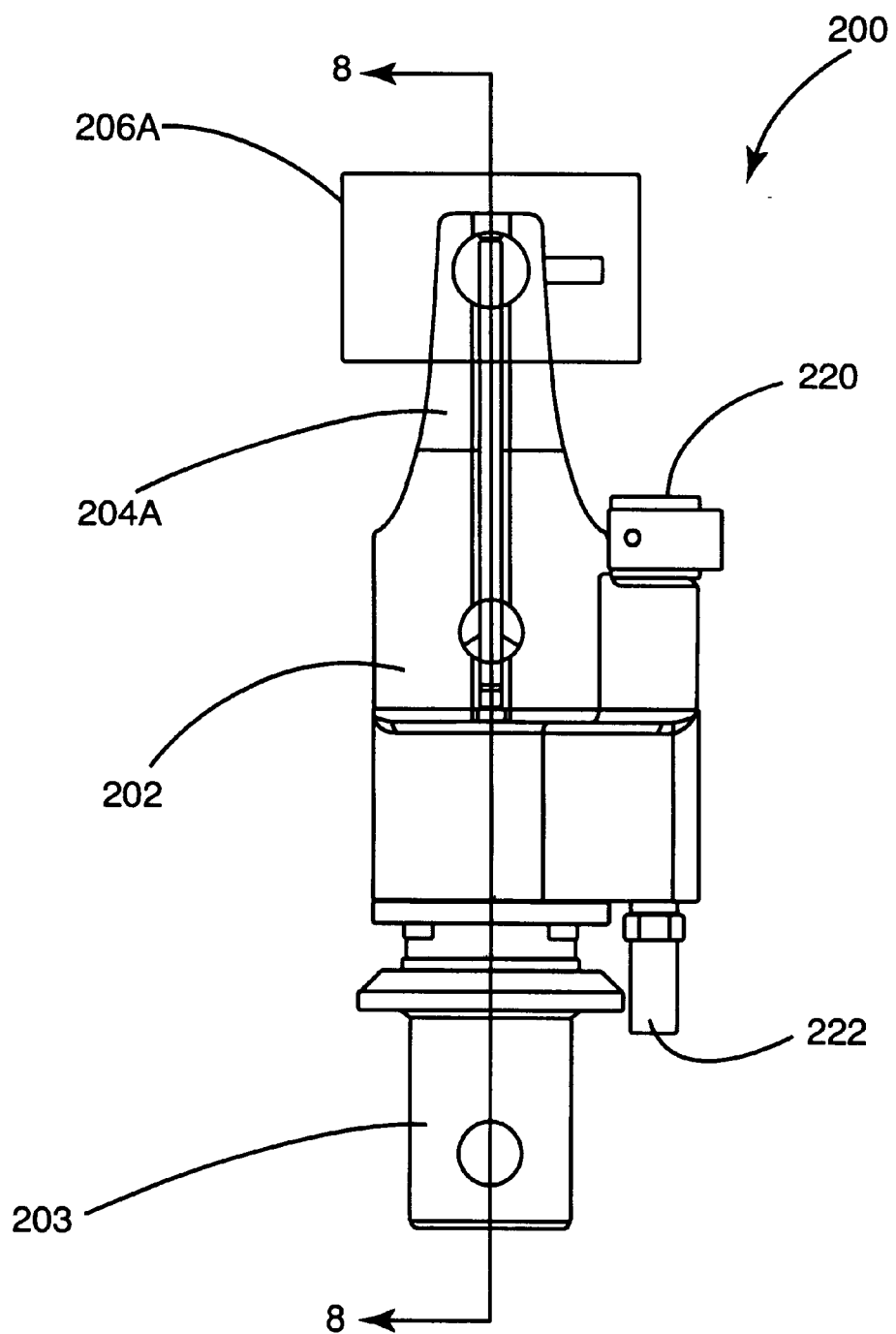
FIG. 7 illustrates a side view of an alternative embodiment of a test specimen holder according to the present invention.
Figure 8:
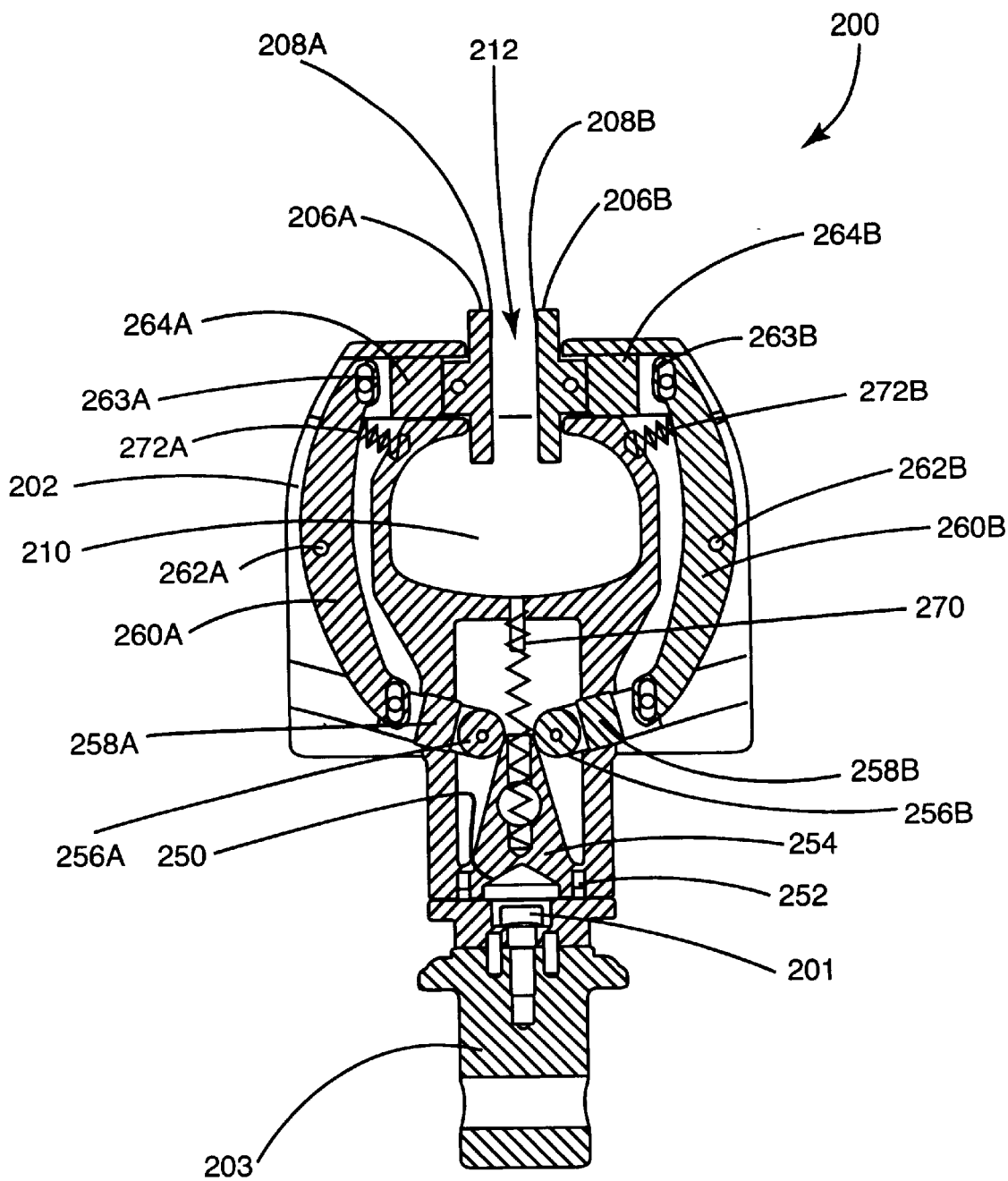
FIG. 8 is a section view of the test specimen holder illustrated in FIG. 7 taken along line 8—8 of FIG. 7.

As appreciated by those skilled in the art, alternative test specimen holder designs may be used with the present invention. FIGS. 7 and 8 illustrate an alternative test specimen holder according to the present invention. FIG. 7 is a side view of holder 200 and FIG. 8 is a section view of the holder 200 taken along line 8—8 in FIG. 7. Holder 200 includes base member 202 and alignment member 203. Base member 202 and alignment member 203 are fastened together with fastener 201. Alignment member 203 is couplable to a material testing system. Sidewall portions 204A and 204B are connected to base member 202 and form recess 210. Jaws 206A and 206B are provided on sidewall portions 204A and 204B, respectively. Each jaw 206A and 206B includes gripping surface 208A and 208B adapted to engage a test specimen inserted through access aperture 212. Jaws 206A and 206B are operably coupled to user operable knob 220 in order to engage a test specimen.

User operable knob 220 controls fluid passed into piston chamber 250 enclosed in base member 202 through port 222. Seal 252 prevents the unwanted entry or exit of fluid from piston chamber 250. Changes in fluid pressure within piston chamber 250 moves piston 254 relative to piston chamber 250 depending upon operation of user operable knob 220. An increase in fluid pressure within piston chamber 250 urges piston 254 to move toward jaws 206A and 206B. This movement causes piston 254 to slide along rollers 256A and 256B and urge rollers 256A and 256B away from each other. As rollers 256A and 256B move away from each other, slides 258A and 258B urge jaw actuators 260A and 260B. In particular, slides 258A and 258B cause jaw actuators 260A and 260B to pivot about pivots 262A and 262B. As jaw actuators 260A and 260B pivot about pivots 262A and 262B, upper portions 263A and 263B of jaw actuators 260A and 260B urge jaw slides 264A and 264B toward each other. Upper portions 263A and 263B cause jaw slides 264A and 264B to move jaws 206A and 206B toward each other.

Upon a decrease in fluid pressure in piston chamber 250, piston 254 is urged away from jaws 206A and 206B. Resilient member 270 aids in urging piston 254 away from jaws 206A and 206B relative to piston chamber 250. Upon movement of piston 254 away from jaws 206A and 206B relative to piston chamber 250, rollers 256A and 256B are urged toward each other. Slides 258A and 258B also move toward each other. This allows jaw actuators 260A and 260B to pivot freely about pivots 262A and 262B. In addition, resilient members 272A and 272B aid in pivoting jaw actuators 260A and 260B such that upper portions 263A and 263B are urged away from jaw slides 264A and 264B. Ultimately, jaws 206A and 206B move away from each other.

Although the present invention has been described with reference to illustrative embodiments, workers skilled in the art will recognize that changes may be made in form and detail without departing from the spirit and scope of the invention.

What is claimed is:

1. A test specimen holder for holding a test specimen in a material testing machine applying force loads, the test specimen holder comprising:

a base member having a piston chamber, a valve chamber fluidly coupled to the piston chamber, a port fluidly coupled to the valve chamber and an end couplable to the material testing machine;

a piston movable relative to the piston chamber;

a pair of first and second jaw assemblies supported by the base member so as to be opposite each other, the jaw assemblies being operably coupled to the piston;

a valve disposed in the valve chamber;

a valve stem supported by the base member and coupled to the valve, the valve stem being twistable to operate the valve in order to minimize unwanted preloading of a test specimen secured by the test specimen holder; and a user operable knob coupled to the valve stem.

2. The test specimen holder of claim 1 wherein the valve is linearly slidable in the valve chamber to selectively fluidly couple the port to the piston chamber.

3. The test specimen holder of claim 2 wherein the valve stem includes a cam surface engaging the valve.

4. The test specimen holder of claim 3 wherein an axis of rotation of the valve stem is parallel to a central axis of the valve chamber.

5. The test specimen holder of claim 4 wherein the base member includes an access opening through which a test specimen is inserted to be engaged by the jaw assemblies, the user operable knob being disposed so as to be below the access opening when the base assembly is oriented such that the access opening is above the end of the base member.

6. The test specimen holder of claim 1 and further comprising a resilient member operably coupled to the piston.

7. A test specimen holder for holding a test specimen in a material testing machine applying force loads, the test specimen holder comprising:

a base member having a piston chamber, a port and an end couplable to the material testing machine;

a piston movable in the piston chamber;

a pair of first and second jaw assemblies supported by the base member so as to be opposite each other, the jaw assemblies being operably coupled to the piston; and valve means for selectively, fluidly coupling the port to the piston chamber, the valve means comprising a twistable user operable knob disposed on the base member in order to minimize unwanted preloading of a test specimen secured by the test specimen holder.

8. The test specimen holder of claim 6 wherein the valve means includes a valve stem coupled to the user operable knob and rotatable in the base member, the valve stem having a cam surface.

9. A test specimen holder for holding a test specimen in a material testing machine applying force loads, the test specimen holder comprising:

a base member having a piston chamber;

an end plate coupled to the base member to enclose the piston chamber;

an alignment member coupled to the end plate to align the base member with the material testing machine, the alignment member being couplable to the material testing machine;

a piston movable relative to the piston chamber;

a pair of first and second jaw assemblies supported by the base member so as to be opposite each other, the jaw assemblies being operably coupled to the piston;

a valve chamber fluidly coupled to the piston chamber and coupled to the material testing machine;

a valve stem supported by the base member coupled to the valve, the valve stem being twistable to operate the valve in order to minimize unwanted preloading of a test specimen secured by the test specimen holder; and a user operable knob coupled to the valve stem.

* * * * *